US009511236B2

(12) United States Patent
Varady et al.

(10) Patent No.: US 9,511,236 B2
(45) Date of Patent: Dec. 6, 2016

(54) LEADLESS CARDIAC PACEMAKER WITH INTEGRAL BATTERY AND REDUNDANT WELDS

(71) Applicant: Pacesetter, Inc., Sunnyvale, CA (US)

(72) Inventors: Eric Varady, San Francisco, CA (US); Alan Ostroff, Pleasanton, CA (US); Peter M. Jacobson, Livermore, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 531 days.

(21) Appl. No.: 13/669,242

(22) Filed: Nov. 5, 2012

(65) Prior Publication Data

US 2013/0123875 A1    May 16, 2013

Related U.S. Application Data

(60) Provisional application No. 61/555,988, filed on Nov. 4, 2011.

(51) Int. Cl.
*A61N 1/375* (2006.01)
*A61N 1/372* (2006.01)
(Continued)

(52) U.S. Cl.
CPC ............. *A61N 1/3756* (2013.01); *A61N 1/375* (2013.01); *A61N 1/3752* (2013.01);
(Continued)

(58) Field of Classification Search
CPC .... A61N 1/3756; A61N 1/375; A61N 1/3752; A61N 1/3754; A61N 1/3758; A61N 1/37205; A61N 1/3968; A61N 1/056; B23K 26/206
See application file for complete search history.

(56) References Cited

U.S. PATENT DOCUMENTS 3,199,508 A    8/1965    Roth
3,212,496 A    10/1965    Preston
(Continued)

FOREIGN PATENT DOCUMENTS

EP    0 801 958 A1    10/1997
EP    1741465 A1    1/2007
(Continued)

OTHER PUBLICATIONS

U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of this app. is U.S. Pat. No. 7,630,767).
(Continued)

*Primary Examiner* — Tammie K Heller
(74) *Attorney, Agent, or Firm* — Theresa A. Raymer (57) ABSTRACT

A leadless cardiac pacemaker that does not require a separate hermetic housing surrounding the battery and electronics compartments is provided. The cardiac pacemaker can include a battery disposed in a battery housing and a set of electronics disposed in an electronics housing. In some embodiments, the battery housing and the electronics housing can comprise an external surface of the pacemaker. The pacemaker can include a first set of welds separating the battery from the set of electronics, and a second set of welds separating the set of electronics and the battery from an exterior of the housing. Various embodiments for achieving dual-redundant welds are also provided.

25 Claims, 8 Drawing Sheets

(51) Int. Cl.
  *A61N 1/39* (2006.01)
  *B23K 26/20* (2014.01)
(52) U.S. Cl.
  CPC ....... *A61N 1/37205* (2013.01); *A61N 1/3968* (2013.01); *B23K 26/206* (2013.01)

(56) References Cited

U.S. PATENT DOCUMENTS

| | | |
|---|---|---|
| 3,218,638 A | 11/1965 | Honig |
| 3,241,556 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner |
| 3,835,864 A | 9/1974 | Rasor et al. |
| 3,836,798 A | 9/1974 | Greatbatch |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson et al. |
| 3,943,926 A | 3/1976 | Barragan |
| 3,946,744 A | 3/1976 | Auerbach |
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,102,344 A | 7/1978 | Conway et al. |
| 4,146,029 A | 3/1979 | Ellinwood, Jr. |
| 4,151,513 A | 4/1979 | Menken et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Hepp et al. |
| 4,210,149 A | 7/1980 | Heilman et al. |
| RE30,366 E | 8/1980 | Rasor et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,458,692 A | 7/1984 | Simson |
| 4,481,950 A | 11/1984 | Duggan |
| 4,513,743 A | 4/1985 | van Arragon et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold, Jr. et al. |
| 4,543,955 A | 10/1985 | Schroeppel |
| 4,550,370 A | 10/1985 | Baker |
| 4,552,127 A | 11/1985 | Schiff |
| 4,552,154 A | 11/1985 | Hartlaub |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A | 3/1989 | Causey, III et al. |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,858,610 A | 8/1989 | Callaghan et al. |
| 4,860,750 A | 8/1989 | Frey et al. |
| 4,875,483 A | 10/1989 | Vollmann et al. |
| 4,880,004 A | 11/1989 | Baker, Jr. et al. |
| 4,883,064 A | 11/1989 | Olson et al. |
| 4,886,064 A | 12/1989 | Strandberg |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,974,589 A | 12/1990 | Sholder |
| 4,987,897 A | 1/1991 | Funke |
| 4,995,390 A | 2/1991 | Cook et al. |
| 5,010,887 A | 4/1991 | Thornander |
| 5,012,806 A | 5/1991 | De Bellis |
| 5,014,701 A | 5/1991 | Pless et al. |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,109,845 A | 5/1992 | Yuuchi et al. |
| 5,111,816 A | 5/1992 | Pless et al. |
| 5,113,859 A | 5/1992 | Funke |
| 5,113,869 A | 5/1992 | Nappholz et al. |
| 5,133,350 A | 7/1992 | Duffin |
| 5,135,004 A | 8/1992 | Adams et al. |
| 5,170,784 A | 12/1992 | Ramon et al. |
| 5,170,802 A | 12/1992 | Mehra |
| 5,179,947 A | 1/1993 | Meyerson et al. |
| 5,184,616 A | 2/1993 | Weiss |
| 5,193,539 A | 3/1993 | Schulman et al. |
| 5,193,540 A | 3/1993 | Schulman et al. |
| 5,193,550 A | 3/1993 | Duffin |
| 5,217,010 A | 6/1993 | Tsitlik et al. |
| 5,247,945 A | 9/1993 | Heinze et al. |
| 5,259,394 A | 11/1993 | Bens |
| 5,267,150 A | 11/1993 | Wilkinson |
| 5,282,841 A | 2/1994 | Szyszkowski |
| 5,284,136 A | 2/1994 | Hauck et al. |
| 5,291,902 A | 3/1994 | Carman |
| 5,300,093 A | 4/1994 | Koestner et al. |
| 5,304,206 A | 4/1994 | Baker, Jr. et al. |
| 5,304,209 A | 4/1994 | Adams et al. |
| 5,313,953 A | 5/1994 | Yomtov et al. |
| 5,318,596 A | 6/1994 | Barreras et al. |
| 5,331,966 A | 7/1994 | Bennett et al. |
| 5,333,095 A | 7/1994 | Stevenson et al. |
| 5,336,244 A | 8/1994 | Weijand |
| 5,342,401 A | 8/1994 | Spano et al. |
| 5,354,317 A | 10/1994 | Alt |
| 5,358,514 A | 10/1994 | Schulman et al. |
| 5,373,852 A | 12/1994 | Harrison et al. |
| 5,383,912 A | 1/1995 | Cox et al. |
| 5,383,915 A | 1/1995 | Adams |
| 5,404,877 A | 4/1995 | Nolan et al. |

(56) References Cited

U.S. PATENT DOCUMENTS

| | | |
|---|---|---|
| 5,405,367 A | 4/1995 | Schulman et al. |
| 5,406,444 A | 4/1995 | Selfried et al. |
| 5,411,532 A | 5/1995 | Mortazavi |
| 5,411,535 A | 5/1995 | Fujii |
| 5,411,537 A | 5/1995 | Munshi et al. |
| 5,417,222 A | 5/1995 | Dempsey et al. |
| 5,419,337 A | 5/1995 | Dempsey et al. |
| 5,431,171 A | 7/1995 | Harrison et al. |
| 5,446,447 A | 8/1995 | Carney et al. |
| 5,456,261 A | 10/1995 | Luczyk |
| 5,466,246 A | 11/1995 | Silvian |
| 5,469,857 A | 11/1995 | Laurent et al. |
| 5,480,415 A | 1/1996 | Cox et al. |
| 5,481,262 A | 1/1996 | Urbas et al. |
| 5,522,876 A | 6/1996 | Rusink |
| 5,531,779 A | 7/1996 | Dahl et al. |
| 5,531,781 A | 7/1996 | Alferness et al. |
| 5,531,783 A | 7/1996 | Giele et al. |
| 5,539,775 A | 7/1996 | Tuttle et al. |
| 5,549,654 A | 8/1996 | Powell |
| 5,549,659 A | 8/1996 | Johansen et al. |
| 5,551,427 A | 9/1996 | Altman |
| 5,556,421 A | 9/1996 | Prutchi et al. |
| 5,562,717 A | 10/1996 | Tippey et al. |
| 5,571,143 A | 11/1996 | Hoegnelid et al. |
| 5,571,148 A | 11/1996 | Loeb et al. |
| 5,579,775 A | 12/1996 | Dempsey et al. |
| 5,586,556 A | 12/1996 | Spivey et al. |
| 5,591,217 A | 1/1997 | Barreras |
| 5,598,848 A | 2/1997 | Swanson et al. |
| 5,649,952 A | 7/1997 | Lam |
| 5,650,759 A | 7/1997 | Hittman et al. |
| 5,654,984 A | 8/1997 | Hershbarger et al. |
| 5,662,689 A | 9/1997 | Elsberry et al. |
| 5,669,391 A | 9/1997 | Williams |
| 5,674,259 A | 10/1997 | Gray |
| 5,676,153 A | 10/1997 | Smith et al. |
| 5,693,076 A | 12/1997 | Kaemmerer |
| 5,694,940 A | 12/1997 | Unger et al. |
| 5,694,952 A | 12/1997 | Lidman et al. |
| 5,697,958 A | 12/1997 | Paul et al. |
| 5,702,427 A | 12/1997 | Ecker et al. |
| 5,725,559 A | 3/1998 | Alt et al. |
| 5,728,154 A | 3/1998 | Crossett et al. |
| 5,730,143 A | 3/1998 | Schwarzberg |
| 5,735,880 A | 4/1998 | Prutchi et al. |
| 5,738,102 A | 4/1998 | Lemelson |
| 5,740,811 A | 4/1998 | Hedberg et al. |
| 5,741,314 A | 4/1998 | Daly et al. |
| 5,766,231 A | 6/1998 | Erickson et al. |
| 5,792,205 A | 8/1998 | Alt et al. |
| 5,810,735 A | 9/1998 | Halperin et al. |
| 5,814,076 A | 9/1998 | Brownlee |
| 5,814,087 A | 9/1998 | Renirie |
| 5,814,089 A | 9/1998 | Stokes et al. |
| 5,824,016 A | 10/1998 | Ekwall |
| 5,871,451 A | 2/1999 | Unger et al. |
| 5,876,353 A | 3/1999 | Riff |
| 5,876,425 A | 3/1999 | Gord et al. |
| 5,891,178 A | 4/1999 | Mann et al. |
| 5,899,928 A | 5/1999 | Sholder et al. |
| 5,935,079 A | 8/1999 | Swanson et al. |
| 5,954,761 A | 9/1999 | Machek et al. |
| 5,957,861 A | 9/1999 | Combs et al. |
| 5,984,861 A | 11/1999 | Crowley |
| 5,987,352 A | 11/1999 | Klein et al. |
| 5,995,876 A | 11/1999 | Kruse et al. |
| 5,999,857 A | 12/1999 | Weijand et al. |
| 6,002,969 A | 12/1999 | Machek et al. |
| 6,004,269 A | 12/1999 | Crowley et al. |
| 6,061,596 A | 5/2000 | Richmond et al. |
| 6,076,016 A | 6/2000 | Feierbach |
| 6,080,187 A | 6/2000 | Alt et al. |
| 6,093,146 A | 7/2000 | Filangeri |
| 6,096,065 A | 8/2000 | Crowley |
| 6,102,874 A | 8/2000 | Stone et al. |
| 6,112,116 A | 8/2000 | Fischell et al. |
| 6,115,628 A | 9/2000 | Stadler et al. |
| 6,115,630 A | 9/2000 | Stadler et al. |
| 6,115,636 A | 9/2000 | Ryan |
| 6,119,031 A | 9/2000 | Crowley |
| 6,125,290 A | 9/2000 | Miesel |
| 6,125,291 A | 9/2000 | Miesel et al. |
| 6,128,526 A | 10/2000 | Stadler et al. |
| 6,129,751 A | 10/2000 | Lucchesi et al. |
| 6,132,390 A | 10/2000 | Cookston et al. |
| 6,132,456 A | 10/2000 | Sommer et al. |
| 6,134,459 A | 10/2000 | Roberts et al. |
| 6,134,470 A | 10/2000 | Hartlaub |
| 6,139,510 A | 10/2000 | Palermo |
| 6,141,584 A | 10/2000 | Rockwell et al. |
| 6,141,588 A | 10/2000 | Cox et al. |
| 6,141,592 A | 10/2000 | Pauly |
| 6,144,866 A | 11/2000 | Miesel et al. |
| 6,148,230 A | 11/2000 | KenKnight |
| 6,152,882 A | 11/2000 | Prutchi |
| 6,163,723 A | 12/2000 | Roberts et al. |
| 6,164,284 A | 12/2000 | Schulman et al. |
| 6,167,310 A | 12/2000 | Grevious |
| 6,178,349 B1 | 1/2001 | Kieval |
| 6,178,356 B1 | 1/2001 | Chastain et al. |
| 6,185,443 B1 | 2/2001 | Crowley |
| 6,185,452 B1 | 2/2001 | Schulman et al. |
| 6,185,464 B1 | 2/2001 | Bonner et al. |
| 6,188,932 B1 | 2/2001 | Lindegren |
| 6,190,324 B1 | 2/2001 | Kieval et al. |
| 6,198,952 B1 | 3/2001 | Miesel |
| 6,201,993 B1 | 3/2001 | Kruse et al. |
| 6,208,894 B1 | 3/2001 | Schulman et al. |
| 6,208,900 B1 | 3/2001 | Ecker et al. |
| 6,223,081 B1 | 4/2001 | Kerver |
| 6,230,059 B1 | 5/2001 | Duffin |
| 6,236,882 B1 | 5/2001 | Lee et al. |
| 6,240,321 B1 | 5/2001 | Janke et al. |
| 6,243,608 B1 | 6/2001 | Pauly et al. |
| 6,248,080 B1 | 6/2001 | Miesel et al. |
| 6,263,245 B1 | 7/2001 | Snell |
| 6,265,100 B1 | 7/2001 | Saaski et al. |
| 6,266,554 B1 | 7/2001 | Hsu et al. |
| 6,266,564 B1 | 7/2001 | Hill et al. |
| 6,272,379 B1 | 8/2001 | Fischell et al. |
| 6,280,409 B1 | 8/2001 | Stone et al. |
| 6,289,229 B1 | 9/2001 | Crowley |
| 6,306,088 B1 | 10/2001 | Krausman et al. |
| 6,310,960 B1 | 10/2001 | Saaski et al. |
| 6,315,721 B2 | 11/2001 | Schulman et al. |
| 6,324,418 B1 | 11/2001 | Crowley et al. |
| 6,324,421 B1 | 11/2001 | Stadler et al. |
| RE37,463 E | 12/2001 | Altman |
| 6,343,227 B1 | 1/2002 | Crowley |
| 6,343,233 B1 | 1/2002 | Werner et al. |
| 6,347,245 B1 | 2/2002 | Lee et al. |
| 6,358,202 B1 | 3/2002 | Arent |
| 6,361,522 B1 | 3/2002 | Scheiner et al. |
| 6,363,282 B1 | 3/2002 | Nichols et al. |
| 6,364,831 B1 | 4/2002 | Crowley |
| 6,370,434 B1 | 4/2002 | Zhang et al. |
| 6,381,492 B1 | 4/2002 | Rockwell et al. |
| 6,381,493 B1 | 4/2002 | Stadler et al. |
| 6,381,494 B1 | 4/2002 | Gilkerson et al. |
| 6,383,209 B1 | 5/2002 | Crowley |
| 6,385,593 B2 | 5/2002 | Linberg |
| 6,386,882 B1 | 5/2002 | Linberg |
| 6,397,100 B2 | 5/2002 | Stadler et al. |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott |
| 6,412,490 B1 | 7/2002 | Lee |
| 6,418,346 B1 | 7/2002 | Nelson et al. |
| 6,423,056 B1 | 7/2002 | Ishikawa et al. |
| 6,424,866 B2 | 7/2002 | Mika et al. |
| 6,428,484 B1 | 8/2002 | Battmer et al. |

(56) References Cited

U.S. PATENT DOCUMENTS

| | | |
|---|---|---|
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,442,433 B1 | 8/2002 | Linberg |
| 6,444,970 B1 | 9/2002 | Barbato |
| 6,445,953 B1 | 9/2002 | Bulkes et al. |
| 6,458,145 B1 | 10/2002 | Ravenscroft et al. |
| 6,459,928 B2 | 10/2002 | Mika et al. |
| 6,459,937 B1 | 10/2002 | Morgan et al. |
| 6,466,820 B1 | 10/2002 | Juran et al. |
| 6,468,263 B1 | 10/2002 | Fischell et al. |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 | 11/2002 | Thompson et al. |
| 6,480,733 B1 | 11/2002 | Turcott |
| 6,482,154 B1 | 11/2002 | Haubrich et al. |
| 6,484,055 B1 | 11/2002 | Marcovecchio |
| 6,484,057 B2 | 11/2002 | Ideker et al. |
| 6,490,487 B1 | 12/2002 | Kraus et al. |
| 6,496,715 B1 | 12/2002 | Lee et al. |
| 6,498,951 B1 | 12/2002 | Larson et al. |
| 6,500,168 B1 | 12/2002 | Jellie |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |
| 6,522,928 B2 | 2/2003 | Whitehurst et al. |
| 6,539,257 B1 | 3/2003 | KenKnight |
| 6,542,781 B1 | 4/2003 | Koblish et al. |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten |
| 6,574,509 B1 | 6/2003 | Kraus et al. |
| 6,574,511 B2 | 6/2003 | Lee |
| 6,580,946 B2 | 6/2003 | Struble |
| 6,580,948 B2 | 6/2003 | Haupert et al. |
| 6,584,351 B1 | 6/2003 | Ekwall |
| 6,584,352 B2 | 6/2003 | Combs et al. |
| 6,589,187 B1 | 7/2003 | Dirnberger et al. |
| 6,592,518 B2 | 7/2003 | Denker et al. |
| 6,594,523 B1 | 7/2003 | Levine |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B2 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,697,677 B2 | 2/2004 | Dahl et al. |
| 6,699,200 B2 | 3/2004 | Cao et al. |
| 6,702,857 B2 | 3/2004 | Brauker et al. |
| 6,704,602 B2 | 3/2004 | Berg et al. |
| 6,711,440 B2 | 3/2004 | Deal et al. |
| 6,716,238 B2 | 4/2004 | Elliott |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,728,576 B2 | 4/2004 | Thompson et al. |
| 6,731,976 B2 | 5/2004 | Penn et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2 | 8/2004 | Verness |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |
| 6,813,519 B2 | 11/2004 | Lebel et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,856,835 B2 | 2/2005 | Bardy et al. |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Grill et al. |
| 6,912,420 B2 | 6/2005 | Scheiner et al. |
| 6,917,833 B2 | 7/2005 | Denker et al. |
| 6,922,330 B2 * | 7/2005 | Nielsen ............... A61N 1/375 29/25.03 |
| 6,925,328 B2 | 8/2005 | Foster et al. |
| 6,931,327 B2 | 8/2005 | Goode, Jr. et al. |
| 6,999,821 B2 | 2/2006 | Jenney et al. |
| 7,001,372 B2 | 2/2006 | Richter |
| 7,023,359 B2 | 4/2006 | Goetz et al. |
| 7,027,876 B2 | 4/2006 | Casavant et al. |
| 7,103,408 B2 * | 9/2006 | Haller ............... A61N 1/3605 607/2 |
| 7,120,992 B2 * | 10/2006 | He ............... A61N 1/3605 174/255 |
| 7,146,222 B2 | 12/2006 | Boling |
| 7,146,225 B2 | 12/2006 | Guenst et al. |
| 7,164,950 B2 | 1/2007 | Kroll et al. |
| 7,177,698 B2 | 2/2007 | Klosterman et al. |
| 7,181,505 B2 | 2/2007 | Haller et al. |
| 7,187,971 B2 | 3/2007 | Sommer et al. |
| 7,200,437 B1 | 4/2007 | Nabutovsky et al. |
| 7,212,870 B1 | 5/2007 | Helland |
| 7,277,754 B2 | 10/2007 | McCabe et al. |
| 7,289,853 B1 | 10/2007 | Campbell et al. |
| 7,363,090 B2 | 4/2008 | Halperin et al. |
| 7,558,631 B2 | 7/2009 | Cowan et al. |

(56) References Cited

U.S. PATENT DOCUMENTS

| | | |
|---|---|---|
| 7,565,195 B1 | 7/2009 | Kroll et al. |
| 7,616,991 B2 | 11/2009 | Mann et al. |
| 7,630,767 B1 | 12/2009 | Poore et al. |
| 7,634,313 B1 | 12/2009 | Kroll et al. |
| 7,848,823 B2 | 12/2010 | Drasler et al. |
| 7,937,148 B2 | 5/2011 | Jacobson |
| 7,945,333 B2 | 5/2011 | Jacobson |
| 8,010,209 B2 | 8/2011 | Jacobson |
| 8,295,939 B2 | 10/2012 | Jacobson |
| 8,352,025 B2 | 1/2013 | Jacobson |
| 8,704,124 B2* | 4/2014 | Wilson ............. A61B 17/72 219/121.64 |
| 8,788,035 B2 | 7/2014 | Jacobson |
| 8,798,745 B2 | 8/2014 | Jacobson |
| 2001/0031999 A1 | 10/2001 | Carter et al. |
| 2002/0032467 A1 | 3/2002 | Shemer et al. |
| 2002/0077686 A1 | 6/2002 | Westlund et al. |
| 2002/0116028 A1 | 8/2002 | Greatbatch et al. |
| 2002/0147488 A1 | 10/2002 | Doan et al. |
| 2003/0141995 A1 | 7/2003 | Lin |
| 2003/0158584 A1 | 8/2003 | Cates et al. |
| 2003/0163184 A1 | 8/2003 | Scheiner et al. |
| 2003/0199941 A1* | 10/2003 | Nielsen ............. A61N 1/375 607/36 |
| 2004/0011366 A1 | 1/2004 | Schulman et al. |
| 2004/0059392 A1 | 3/2004 | Parramon et al. |
| 2004/0116939 A1 | 6/2004 | Goode |
| 2004/0133242 A1 | 7/2004 | Chapman et al. |
| 2004/0143262 A1 | 7/2004 | Visram et al. |
| 2004/0147973 A1 | 7/2004 | Hauser |
| 2004/0167587 A1 | 8/2004 | Thompson |
| 2004/0172116 A1 | 9/2004 | Seifert et al. |
| 2004/0193223 A1 | 9/2004 | Kramer et al. |
| 2004/0249417 A1 | 12/2004 | Ransbury et al. |
| 2004/0260349 A1 | 12/2004 | Stroebel |
| 2005/0038474 A1 | 2/2005 | Wool |
| 2005/0038491 A1 | 2/2005 | Haack |
| 2005/0043765 A1 | 2/2005 | Williams et al. |
| 2005/0075682 A1 | 4/2005 | Schulman et al. |
| 2005/0096702 A1 | 5/2005 | Denker et al. |
| 2005/0131478 A1 | 6/2005 | Kim et al. |
| 2005/0149138 A1 | 7/2005 | Min et al. |
| 2005/0165465 A1 | 7/2005 | Pianca et al. |
| 2005/0267555 A1 | 12/2005 | Marnfeldt et al. |
| 2005/0288722 A1 | 12/2005 | Eigler et al. |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0105613 A1 | 5/2006 | Carroll |
| 2006/0108335 A1 | 5/2006 | Zhao et al. |
| 2006/0121475 A1 | 6/2006 | Davids et al. |
| 2006/0135999 A1 | 6/2006 | Bodner et al. |
| 2006/0136004 A1 | 6/2006 | Cowan et al. |
| 2006/0161222 A1 | 7/2006 | Haubrich et al. |
| 2006/0241705 A1 | 10/2006 | Neumann et al. |
| 2006/0247750 A1 | 11/2006 | Seifert et al. |
| 2006/0282150 A1 | 12/2006 | Olson et al. |
| 2007/0016263 A1 | 1/2007 | Armstrong et al. |
| 2007/0043414 A1 | 2/2007 | Fifer et al. |
| 2007/0055184 A1 | 3/2007 | Echt et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0123923 A1 | 5/2007 | Lindstrom et al. |
| 2007/0142709 A1 | 6/2007 | Martone et al. |
| 2007/0179552 A1 | 8/2007 | Dennis et al. |
| 2007/0270675 A1 | 11/2007 | Kane et al. |
| 2007/0276004 A1 | 11/2007 | Hirsch et al. |
| 2007/0276444 A1 | 11/2007 | Gelbart et al. |
| 2007/0293904 A1 | 12/2007 | Gelbart et al. |
| 2008/0004535 A1 | 1/2008 | Smits |
| 2008/0021532 A1 | 1/2008 | Kveen et al. |
| 2008/0039738 A1 | 2/2008 | Dinsmoor et al. |
| 2008/0086168 A1 | 4/2008 | Cahill |
| 2008/0091255 A1 | 4/2008 | Caparso et al. |
| 2008/0119911 A1 | 5/2008 | Rosero |
| 2008/0243218 A1 | 10/2008 | Bottomley et al. |
| 2008/0269591 A1 | 10/2008 | Halperin et al. |
| 2009/0018599 A1 | 1/2009 | Hastings et al. |
| 2009/0082827 A1 | 3/2009 | Kveen et al. |
| 2009/0082828 A1 | 3/2009 | Ostroff |
| 2009/0149902 A1 | 6/2009 | Kumar et al. |
| 2009/0171408 A1 | 7/2009 | Solem |
| 2009/0206066 A1* | 8/2009 | Rekowski ............. B23K 26/082 219/121.81 |
| 2010/0069983 A1 | 3/2010 | Peacock et al. |
| 2010/0198288 A1 | 8/2010 | Ostroff |
| 2010/0211149 A1 | 8/2010 | Morgan et al. |
| 2010/0249828 A1 | 9/2010 | Mavani et al. |
| 2010/0292541 A1 | 11/2010 | Hashiba et al. |
| 2010/0305629 A1 | 12/2010 | Lund et al. |
| 2010/0305653 A1 | 12/2010 | Lund et al. |
| 2010/0305656 A1 | 12/2010 | Imran et al. |
| 2010/0312332 A1 | 12/2010 | Forster et al. |
| 2011/0004117 A1 | 1/2011 | Neville et al. |
| 2011/0071586 A1 | 3/2011 | Jacobson |
| 2011/0077708 A1 | 3/2011 | Ostroff |
| 2011/0190842 A1* | 8/2011 | Johnson et al. ............. 607/37 |
| 2011/0208260 A1 | 8/2011 | Jacobson |
| 2011/0282423 A1 | 11/2011 | Jacobson |
| 2012/0010709 A1* | 1/2012 | Wilson ............. A61B 17/72 623/16.11 |
| 2012/0089198 A1 | 4/2012 | Ostroff |
| 2012/0095539 A1 | 4/2012 | Khairkhahan et al. |
| 2012/0109236 A1 | 5/2012 | Jacobson et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0197373 A1 | 8/2012 | Khairkhahan et al. |
| 2012/0245665 A1 | 9/2012 | Friedman et al. |
| 2012/0255990 A1* | 10/2012 | Szabo ............. B23K 20/124 228/114.5 |
| 2012/0290021 A1* | 11/2012 | Saurkar et al. ............. 607/2 |
| 2013/0041422 A1 | 2/2013 | Jacobson |
| 2013/0261497 A1 | 10/2013 | Pertijs et al. |
| 2013/0274847 A1 | 10/2013 | Ostroff |
| 2013/0324825 A1 | 12/2013 | Ostroff et al. |
| 2014/0039570 A1 | 2/2014 | Carroll et al. |

FOREIGN PATENT DOCUMENTS

| | | |
|---|---|---|
| JP | H04-506167 A | 10/1992 |
| JP | 05-245215 | 9/1993 |
| JP | 06/507096 | 3/2006 |
| JP | 06/516449 | 7/2006 |
| JP | 2006-526483 A | 11/2006 |
| WO | WO93/12714 A1 | 7/1993 |
| WO | WO02/34333 A2 | 5/2002 |
| WO | WO2004/012811 | 2/2004 |
| WO | WO 2006/065394 A1 | 6/2006 |
| WO | WO 2007/047681 A2 | 4/2007 |
| WO | WO 2007/059386 A2 | 5/2007 |
| WO | WO 2008/058265 A2 | 5/2008 |
| WO | WO2010/088116 A1 | 8/2010 |
| WO | 2011/094413 A1 | 8/2011 |

OTHER PUBLICATIONS

Beeby et al.; Micromachined silicon generator for harvesting power from vibrations; (Proceedings) PowerMEMS 2004; Kyoto, Japan; pp. 104-107; Nov. 28-30, 2004.

Bordacher et al.; Impact and prevention of far-field sensing in fallback mode switches; PACE; vol. 26 (pt. II); pp. 206-209; Jan. 2003.

Brandt et al.; Far-field QRS complex sensing: prevalence and timing with bipolar atrial leads; PACE; vol. 23; pp. 315-320; Mar. 2000.

Brown, Eric S.; The atomic battery; Technology Review: Published by MIT; 4 pgs.; Jun. 16, 2005.

Irnich et al.; Do we need pacemakers resistant to magnetic resonance imaging; Europace; vol. 7; pp. 353-365; Feb. 2005.

(56) References Cited

OTHER PUBLICATIONS

Irnich; Electronic security systems and active implantable medical devices; Journal of PACE; vol. 25; No. 8; pp. 1235-1258; Aug. 2002.

Luechinger et al.; Force and torque effects of a 1.5-tesla MRI scanner of cardiac pacemakers and ICDs; Journal of PACE; vol. 24; No. 2; pp. 199-205; Feb. 2001.

Luechinger et al.; In vivo heating of pacemaker leads during magnetic resonance imaging; European Heart Journal; vol. 26; pp. 376-383; Feb. 2005.

Lüchinger ; Safety aspects of cardiac pacemakers in magnetic resonance imaging; Dissertation submitted to the Swiss Federal Institute of Technology Zurich; 137 pages; (year of publication is sufficiently earlier than the effective U.S. filing date and any foreign priority date) 2002.

Nyenhuis et al.; MRI and Implanted Medical Devices: Basic Interactions with an emphasis on heating; vol. 5; No. 3; pp. 467-480; Sep. 2005.

Shellock et al.; Cardiac pacemaker: in vitro assessment at 1.5 T; Am Heart J; vol. 151; No. 2; pp. 436-443; Feb. 2006.

International Searching Authority, "Notification of Transmittal of the International Search Report and the Written Opinion of the International Searching Authority, or the Declaration," International Application No. PCT/US12/63552, Feb. 22, 2013, 11 pages.

\* cited by examiner

LEADLESS CARDIAC PACEMAKER WITH INTEGRAL BATTERY AND REDUNDANT WELDS

CROSS REFERENCE TO RELATED APPLICATIONS

This application claims the benefit of U.S. Provisional Patent Application No. 61/555,988, filed Nov. 4, 2011, titled "Leadless Cardiac Pacemaker with Integral Battery and Redundant Welds", which application is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates to leadless cardiac pacemakers, and more particularly, to features and methods for welding and sealing the battery compartment to miniaturize the leadless pacemaker.

BACKGROUND

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle". Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the related applications cited above.

Self-contained or leadless pacemakers or other biostimulators are typically fixed to an intracardial implant site by an actively engaging mechanism such as a screw or helical member that screws into the myocardium.

Prior leadless pacemakers typically include a sealed battery compartment which is then placed inside another hermetically sealed container. Sealing the battery compartment in a separate housing protects the patient from harm in the event that the battery compartment leaks, but increases the total size of the pacemaker by requiring a separate hermetic housing.

SUMMARY OF THE DISCLOSURE

A leadless cardiac pacemaker is provided, comprising a battery disposed in a battery housing, the battery housing configured to operate as an electrode, a set of electronics disposed in an electronics housing, the set of electronics being electrically coupled to the battery and configured to control operation of the electrode, a first set of welds configured to hermetically seal the battery from the set of electronics, a second set of welds configured to hermetically seal the set of electronics and the battery from an exterior of the leadless cardiac pacemaker, and a fixation device configured to attach the leadless cardiac pacemaker to human tissue.

In some embodiments, the first and second sets of welds provide dual-weld redundancy.

In one embodiment, the battery housing is not surrounded by or enclosed in a separate housing.

In another embodiment, an external surface of the battery housing is also an external surface of the pacemaker.

In one embodiment, the first set of welds is disposed on an interior of the pacemaker and the second set of welds is disposed on the exterior of the pacemaker.

In another embodiment, the battery housing and electronics housing combine to form a cylindrical housing of the pacemaker.

In some embodiments, the battery housing further comprises a cylindrical housing and a lid welded to a distal portion of the battery housing with the first set of welds to hermetically seal the battery housing.

In one embodiment, the battery housing further comprises a cylindrical housing and a first lid welded to a distal portion of the battery housing with the first set of welds to hermetically seal the distal portion of the battery housing, and a second lid welded to a proximal portion of the battery housing with a third set of welds to hermetically seal the proximal portion of the battery housing.

In some embodiments, the device further comprises a cap surrounding the second lid and welded to the battery housing with a fourth set of welds to provide dual-weld redundancy for the proximal end of the housing.

In one embodiment, the battery housing further comprises a lip positioned near a distal end of the battery housing, the lip extending inwards and then distally from an external surface of the battery housing. In another embodiment, the battery housing further comprises an indentation positioned near a distal end of the battery housing, the indentation extending inwards from an external surface of the battery housing.

In one embodiment, the battery housing further comprises a first lip positioned near a distal end of the battery housing and a second lip positioned near a proximal end of the batter housing, the first lip extending inwards and distally from an external surface of the battery housing and the second lip extending inwards and proximally from the external surface of the housing.

In another embodiment, the battery housing further comprises a first indentation positioned near a distal end of the battery housing and a second indentation positioned near a proximal end of the battery housing, the first and second indentations extending inwards from an external surface of the housing.

In some embodiments, the first and second sets of welds are laser bead welds. In another embodiment, the first and second sets of welds are deep-penetration seam welds. In some embodiments, the first set of welds are deep-penetration seam welds and the second set of welds are laser bead welds.

An implantable medical device is provided, comprising a battery disposed in a battery housing, the battery housing comprising an external surface of the implantable medical device, a set of electronics disposed in an electronics housing and electrically coupled to the battery, the set of electronics configured to control operation of the implantable medical device, a first set of welds configured to hermetically seal the battery from the set of electronics, and a second set of welds configured to hermetically seal the set of electronics and the battery from an exterior of the implantable medical device.

In some embodiments, the first and second sets of welds provide dual-weld redundancy.

In one embodiment, the battery housing is not surrounded by or enclosed in a separate housing.

In another embodiment, an external surface of the battery housing is also an external surface of the pacemaker.

In one embodiment, the first set of welds is disposed on an interior of the pacemaker and the second set of welds is disposed on the exterior of the pacemaker.

In another embodiment, the battery housing and electronics housing combine to form a cylindrical housing of the pacemaker.

In some embodiments, the battery housing further comprises a cylindrical housing and a lid welded to a distal portion of the battery housing with the first set of welds to hermetically seal the battery housing.

In one embodiment, the battery housing further comprises a cylindrical housing and a first lid welded to a distal portion of the battery housing with the first set of welds to hermetically seal the distal portion of the battery housing, and a second lid welded to a proximal portion of the battery housing with a third set of welds to hermetically seal the proximal portion of the battery housing.

In some embodiments, the device further comprises a cap surrounding the second lid and welded to the battery housing with a fourth set of welds to provide dual-weld redundancy for the proximal end of the housing.

In one embodiment, the battery housing further comprises a lip positioned near a distal end of the battery housing, the lip extending inwards and then distally from an external surface of the battery housing. In another embodiment, the battery housing further comprises an indentation positioned near a distal end of the battery housing, the indentation extending inwards from an external surface of the battery housing.

In one embodiment, the battery housing further comprises a first lip positioned near a distal end of the battery housing and a second lip positioned near a proximal end of the batter housing, the first lip extending inwards and distally from an external surface of the battery housing and the second lip extending inwards and proximally from the external surface of the housing.

In another embodiment, the battery housing further comprises a first indentation positioned near a distal end of the battery housing and a second indentation positioned near a proximal end of the battery housing, the first and second indentations extending inwards from an external surface of the housing.

In some embodiments, the first and second sets of welds are laser bead welds. In another embodiment, the first and second sets of welds are deep-penetration seam welds. In some embodiments, the first set of welds are deep-penetration seam welds and the second set of welds are laser bead welds.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Implantable leadless cardiac pacemakers or leadless biostimulators typically include a hermetic housing to contain all the necessary electrical components and to prevent any hazardous materials, such as battery electrolyte, from harming a patient in the event of a leak in the housing and/or battery. The hermetic housing can be used to encapsulate both the power source (e.g., battery) as well as the electronics compartment responsible for pacing/sensing of the pacemaker. However, the addition of a hermetic housing increases the size of a leadless biostimulator, making the biostimulator more difficult to implant and more invasive to the patient.

Figures 1A, 1B, 1C:
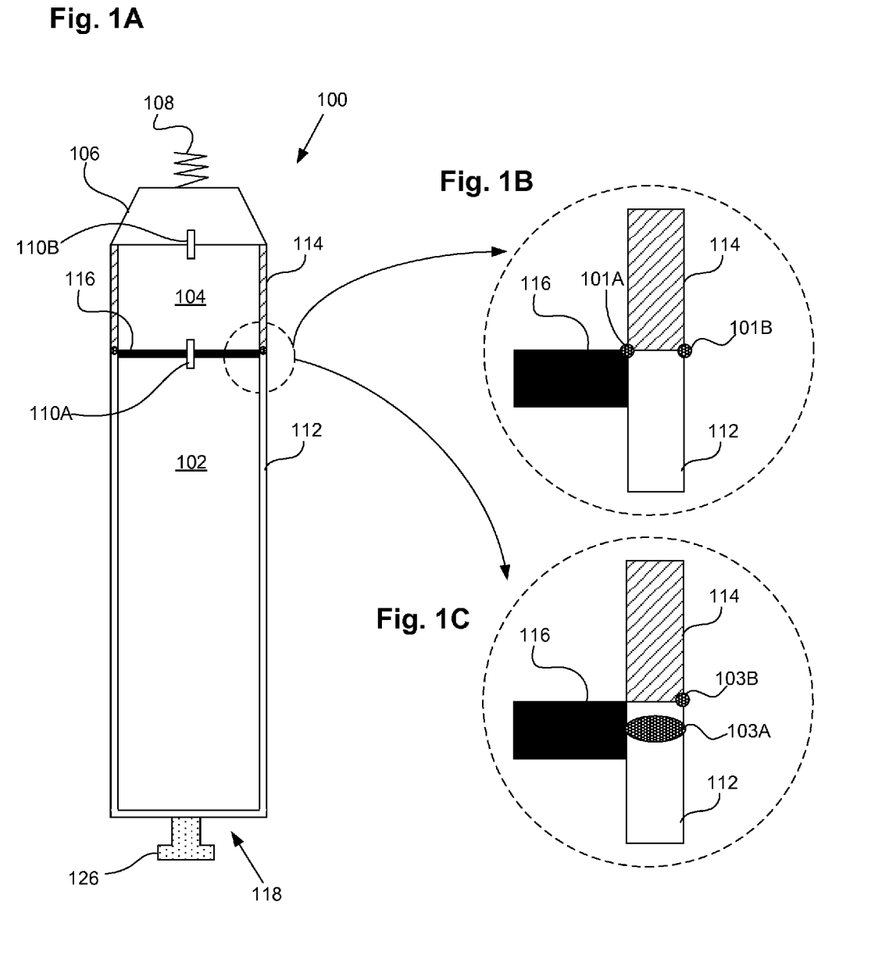
FIGS. 1A-1C illustrate one embodiment of an implantable medical device with dual-redundant welds.

FIGS. 1A-1C shows a leadless cardiac pacemaker or leadless biostimulator 100. The biostimulator includes a hermetic battery 102, electronics compartment 104, header assembly 106, and fixation device 108. The fixation device 108 can be a fixation helix or other flexible or rigid structure suitable for attaching a distal portion of the housing to tissue, such as to heart tissue. In FIG. 1A, a first electrode can be disposed on or integrated within the fixation device 108, and a second electrode can be disposed on the cylindrical wall or can 112 of battery 102, or on electronics compartment 104. Although the specification and drawings herein refer to the can being of a cylindrical shape, it should be understood that in other embodiments, the can or walls of the device can be any other three-dimensional shape, such as a cube, a cuboid, a pyramid, a cone, a hemisphere, and octahedron, etc. In some embodiments, the first electrode may be independent from the fixation device in various forms and sizes. Further details on the components and function of a leadless biostimulator are found in co-pending U.S. application Ser. Nos. 12/568,513 and 11/549,581, which are both incorporated herein by reference.

Standard active implantable devices, such as pacemakers, defibrillators, neurostimulators, cochlear implants, etc, typically have a hermetic battery that is fully contained within another hermetic enclosure. This can be described as a wall-within-a-wall construction, i.e., there are two walls and two welds separating the internal battery electrolyte from the outer patient body fluid. In this situation, two welds must fail in order for the patient to be exposed to battery electrolyte. The enclosures described herein do not comprise this wall-within-a-wall construction. Biostimulator 100 does not include a separate hermetically sealed housing to contain the hermetic battery 102 and electronics compartment 104. Rather, the cylindrical walls 112 and 114 (also referred to herein as "cans") of battery 102 and electronics compartment 104, respectively, make up the outer surface of the biostimulator. Thus, the battery 102 and electronics compartment 104 are not disposed within a separate hermetic housing, so the walls 112 and 114 of the battery and electronics compartment also comprise the outermost surface of the pacemaker.

In some embodiments, lid 116 hermetically separates the battery 102 from the electronics compartment 104. The battery can be coupled to the electronics within the electronics compartment through the battery's hermetic feedthrough 110A, and the electronics can be coupled to the header assembly through the hermetic feedthrough 110B. Constructing the biostimulator 100 without requiring an additional hermetic enclosure to fully enclose the battery and electronics compartment allows the biostimulator to be smaller and lighter than a conventional leadless biostimulator. The resulting biostimulator can then be smaller, thinner, lighter, and less invasive when implanted.

During construction of the biostimulator 100, the various walls/compartments of the biostimulator must be hermetically joined together. Since the walls of the biostimulator are typically made from a conductive, biocompatible, inert, and anodically safe material such as titanium, 316L stainless steel, or other similar materials, welding is an effective technique for joining and sealing the biostimulator. FIGS. 1B-1C show two techniques for welding the cylindrical walls 112 and 114 together with lid 116. In FIG. 1B, weld bead 101A joins walls 112 to 116, and subsequently weld bead 101B joins 112 to 114. In some embodiments, the thickness of wall 112 can be slightly more than the thickness of wall 114 to aid in aligning the cylindrical walls during manufacture. The weld beads can be formed via a laser into a hermetic seam weld, as known in the art. Similarly, in FIG. 1C, a deep-penetration seam weld 103A can be used to join wall 112 to lid 116.

Referring back to FIG. 1A, the proximal portion 118 of the biostimulator 100 can comprise the end of a deep drawn cylinder or machined cylinder so as not to require additional welds at that end. However, any of the welding techniques discussed herein can be used at the proximal portion of the biostimulator if a deep drawn cylinder is not used. A docking assembly 126 may be attached to the proximal portion 118 of the biostimulator.

Figure 2A:
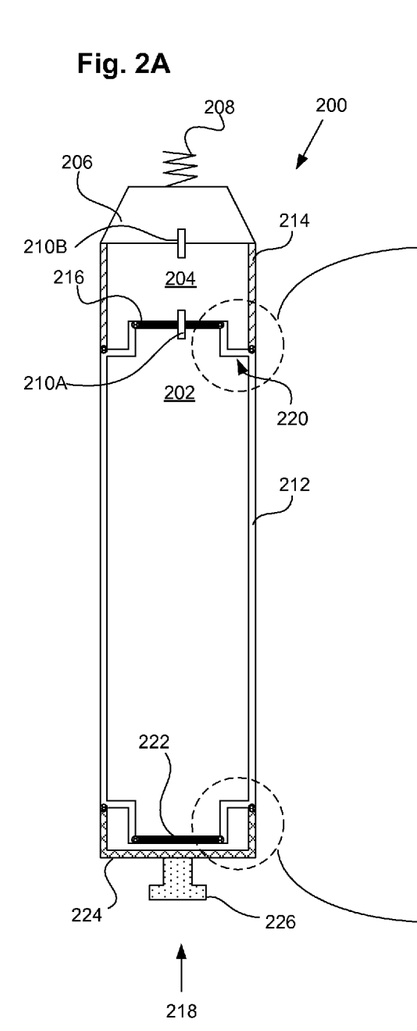
FIGS. 2A-2C illustrate another embodiment of an implantable medical device with dual-redundant welds.
Figure 2B:
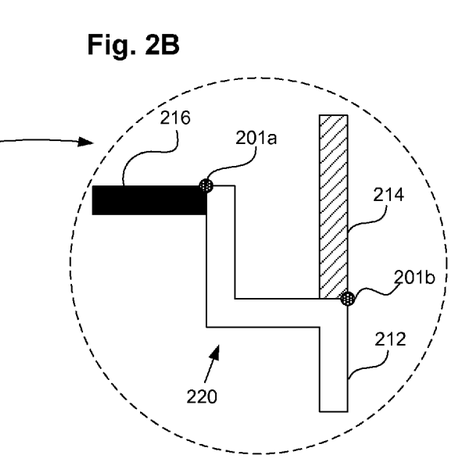
Figure 2C:
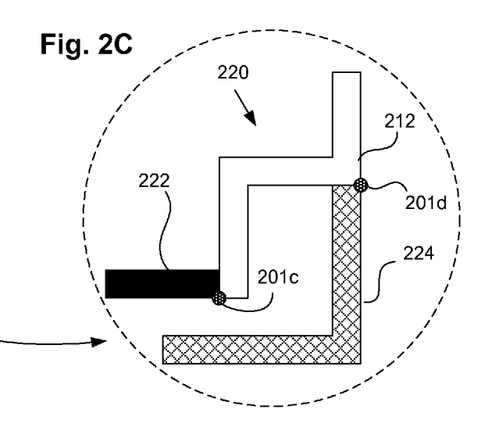

FIGS. 2A-2C illustrate an alternative embodiment of a biostimulator 200 that provides a dual-weld redundancy. Constructing a biostimulator with dual or redundant welds increases the safety of the device within a patient since more than one weld must fail for the patient to be exposed to toxic or harmful components contained within the hermetic battery. The biostimulator 200 can include many of the features described above in FIGS. 1A-1C, including battery 202, electronics compartment 204, header assembly 206, fixation device 208, feedthroughs 210A and 210B, cylindrical walls 212 and 214, and lid 216.

In FIGS. 2A-2C, the walls 212 of the battery 202 can include a lip 220 at the distal (FIG. 2B) and/or proximal (FIG. 2C) portions of the battery. Referring to FIG. 2B, lid 216 can be welded to walls 212 at the inner portion of lip 220 with welds 201a to separate the battery 202 from the electronics compartment 204. Similarly, walls 212 and 214 can be welded together at the outer portion of lip 220 with welds 201b. The proximal portion of the battery may be sealed in a similar manner to the distal portion. In FIG. 2C, lid 222 and walls 212 can be welded together at the inner portion of lip 220 with welds 201c. Similarly, walls 212 and proximal cap 224 can be welded together at the outer portion of lip 220 with welds 201d. Welding the biostimulator in this fashion ensures dual-weld redundancy, requiring failure of the 201a and 201b welds for electrolyte from battery 202 to reach a patient at the distal portion of the battery, or failure of the 201c and 201d welds for electrolyte from battery 202 to reach a patient at the proximal portion of the battery.

The proximal portion 218 of biostimulator 200, as shown in FIGS. 2A and 2C, includes a proximal cap 224 and docking assembly 226. The docking assembly can be configured to engage or be grabbed by a delivery and/or retrieval catheter system for delivery and extraction of the biostimulator to and from tissue. In other embodiments, as described above, the proximal portion 218 of the biostimulator may be formed from a deep drawn enclosure, thus eliminating the need for a lid 222 and proximal cap 224.

Figure 3A:
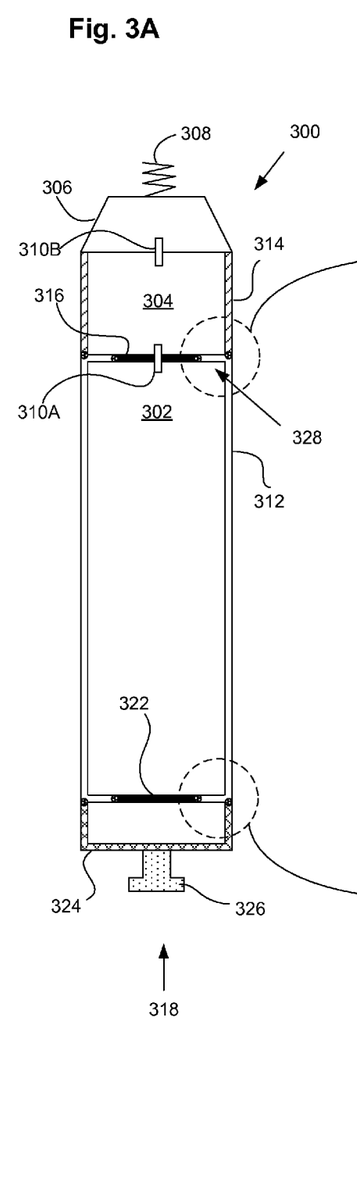
FIGS. 3A-3E illustrate yet another embodiment of an implantable medical device with dual-redundant welds.
Figure 3B:
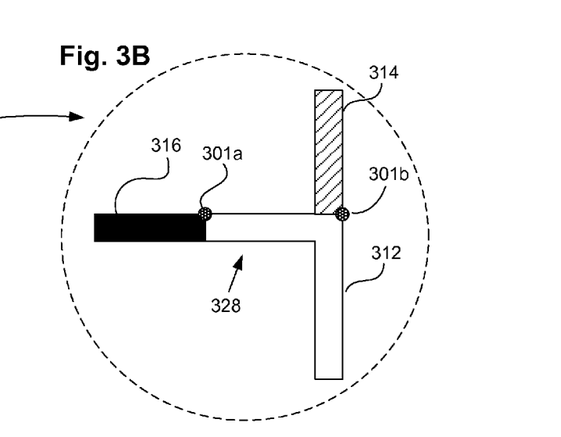
Figure 3C:
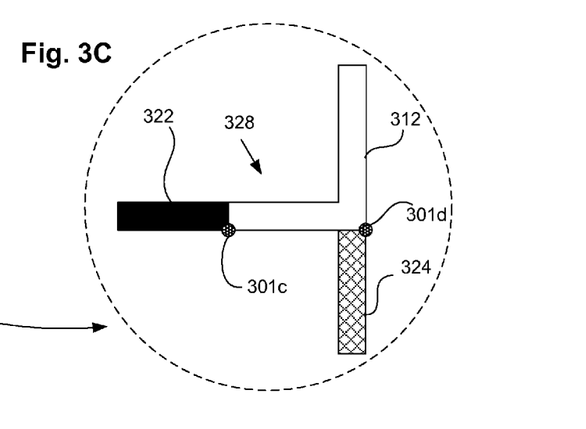

In FIGS. 3A-3C, the walls 312 of the battery 302 can include an indentation 328 at the distal (FIG. 3B) and/or proximal (FIG. 3C) portions of the battery. In some embodiments, the proximal portion of the battery can alternatively be constructed from a deep drawn enclosure. Referring to FIG. 3B, lid 316 can be welded to cylindrical walls 312 at the inner portion of indentation 328 with welds 301a to separate the battery 302 from the electronics compartment 304. Similarly, walls 312 and 314 can be welded together at the outer portion of indentation 328 with welds 301b. The proximal portion of the battery may be sealed in a similar manner to the distal portion. In FIG. 3C, lid 322 and walls 312 can be welded together at the inner portion of indentation 328 with welds 301c. Similarly, walls 312 and proximal cap 324 can be welded together at the outer portion of indentation 328 with welds 301d. Welding the biostimulator in this fashion creates a dual-weld redundancy, which would require failure of the 301a and 301b welds for electrolyte from battery 302 to reach a patient at the distal portion of the battery, or failure of the 301c and 301d welds for electrolyte from battery 302 to reach a patient at the proximal portion of the battery.

Figure 3D:
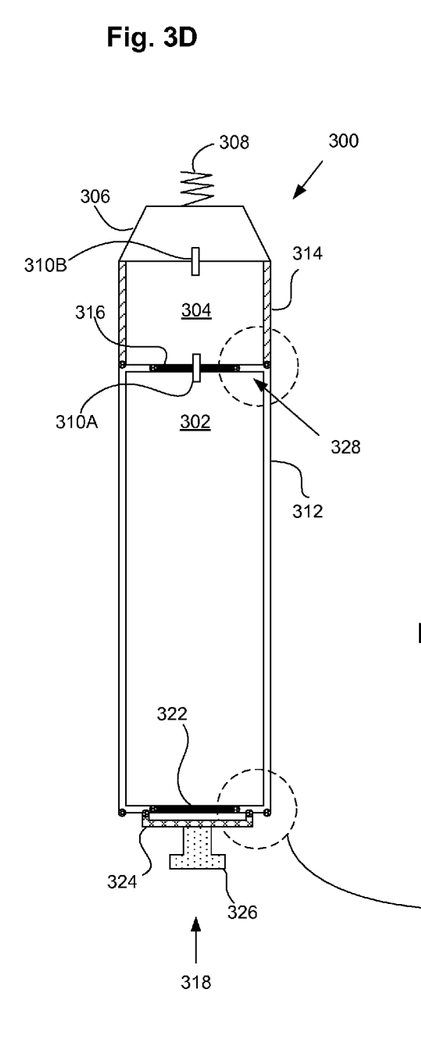
Figure 3E:
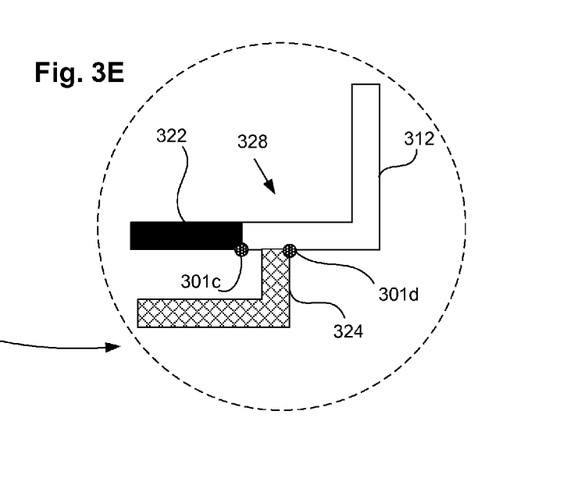

FIGS. 3D-3E illustrate an alternate embodiment of the biostimulator 300 shown in FIGS. 3A-3C. In FIGS. 3D-3E, the proximal cap 324 is only big enough to enclose the lid 322, instead of being welded to the outer portion of indentation 328 as in FIGS. 3A-3C. The proximal cap therefore has a diameter less than the total diameter of walls 312. This provides for a smaller and more compact proximal end cap while still retaining the features of a dual-weld redundancy.

Figure 4A:
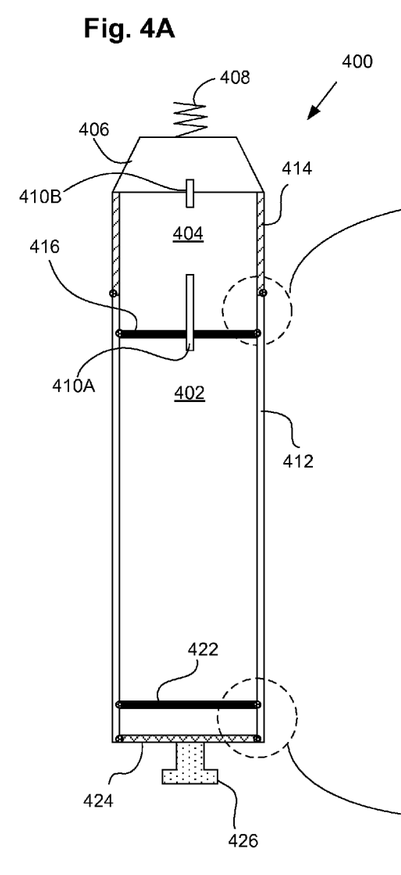
FIGS. 4A-4C illustrate one embodiment of an implantable medical device with dual-redundant welds.
Figure 4B:
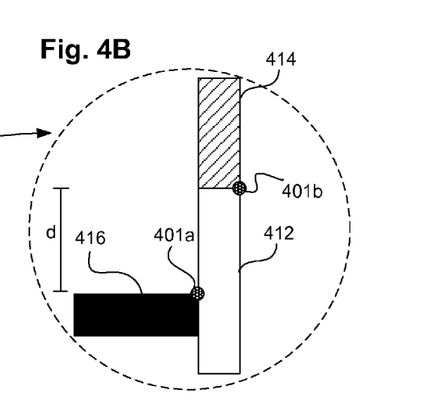
Figure 4C:
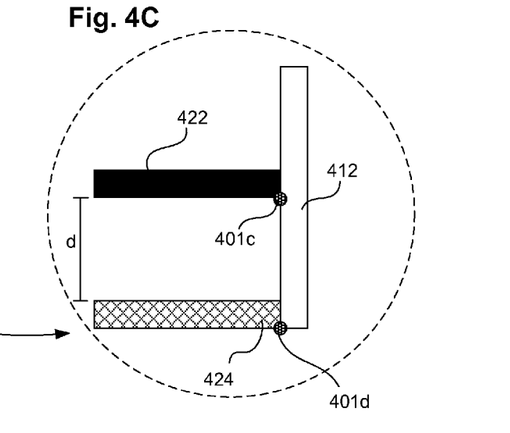

FIGS. 4A-4C illustrate another embodiment of a biostimulator 400 with a dual-weld failure mode. In FIG. 4A, lid 416 is recessed a distance d from the end of walls 412 into the battery compartment. Lid 416 can be recessed inside walls 412 at a distance d and welded in place with weld 401a to separate the battery 402 from the electronics compartment 404. The proximal portion of the battery may be sealed in a similar manner to the distal portion. Lid 422 can be recessed inside at a distance d to the inner portion of walls 412 and welded in place with weld 401c. Proximal cap 424 can then be welded to walls 412 with welds 401d to provide a redundant weld. In some embodiments, lid 422 and proximal cap 424 are not used, but rather, walls 412 are formed from a deep drawn enclosure.

Figure 5A:
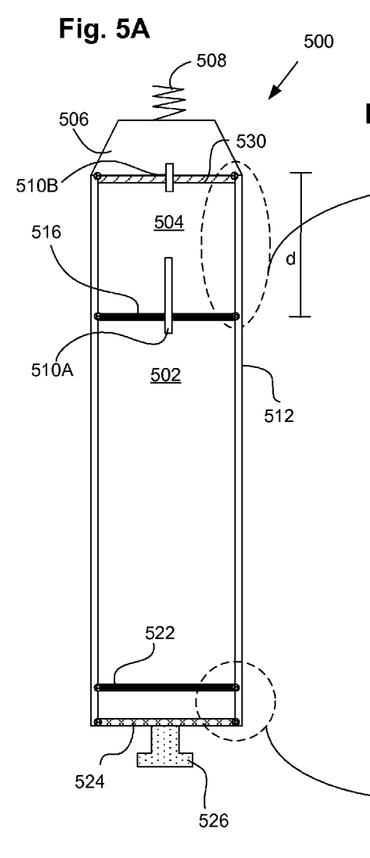
FIGS. 5A-5C illustrate yet another embodiment of an implantable medical device with dual-redundant welds.
Figure 5B:
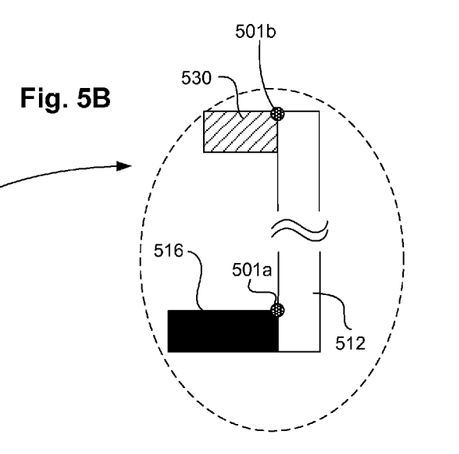
Figure 5C:
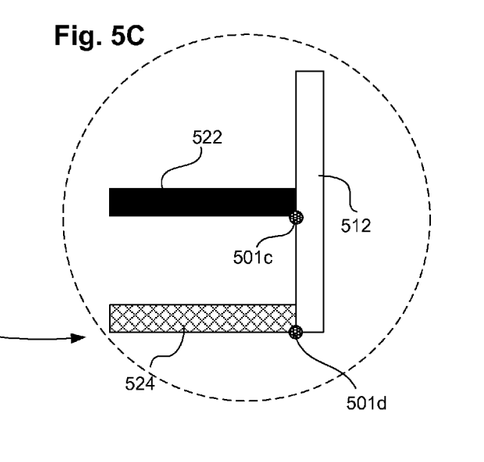

FIGS. 5A-5C illustrate another embodiment of a biostimulator 500 with a dual-weld failure mode. Biostimulator 500 is similar to the biostimulator 400 of FIGS. 4A-4C in that lids 516, 530, 522, and proximal cap 524 are recessed and welded within the cylindrical walls to form the battery 502 and electronics compartment 504. However, in contrast to biostimulator 400 of FIGS. 4A-4C, which included two sets of cylindrical walls or cans 412 and 414, the biostimulator 500 of FIGS. 5A-5C comprises a single cylindrical wall 512 to form both the battery and electrical compartments. The battery and electrical compartments are contained by lids 530, 516, 522, and proximal cap 524. In other embodiments, proximal cap 524 and lid 522 may not be necessary if the can 512 is a deep drawn enclosure, as described above.

In FIG. 5A, lid 516 is recessed a distance d from the end of cylindrical walls 512 into the battery compartment. Lid 516 can be recessed inside walls 512 and welded in place with welds 501a to separate the battery 502 from the electronics compartment 504. Lid 530 can also be recessed inside walls 512 and welded in place with welds 501b to provide a redundant weld.

A feedthrough 510A can pass through lid 516 to couple the battery 502 to the electronics compartment 504, and feedthrough 510B can couple the electronics to the header assembly, as described above. The proximal portion of the battery may be sealed in a similar manner to the distal portion. Lid 522 can be recessed inside cylindrical walls 512 and welded together with welds 501c. Proximal cap 524 can then be welded to walls 512 with welds 501d to provide a redundant weld. In some embodiments, lid 522 and proximal cap 524 are not used, but rather, cylindrical walls or can 512 are formed from a deep drawn enclosure.

Figure 6A:
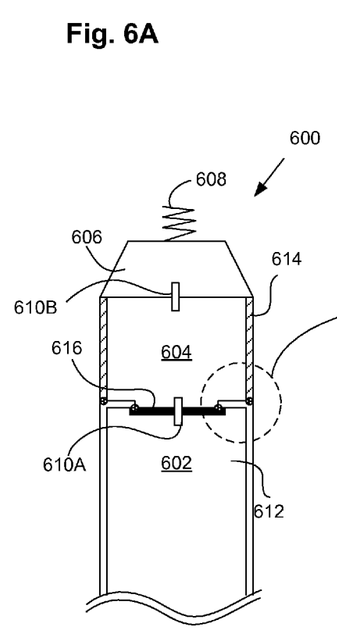
FIGS. 6A-6B illustrate one embodiment of an implantable medical device with dual-redundant welds.
Figure 6B:
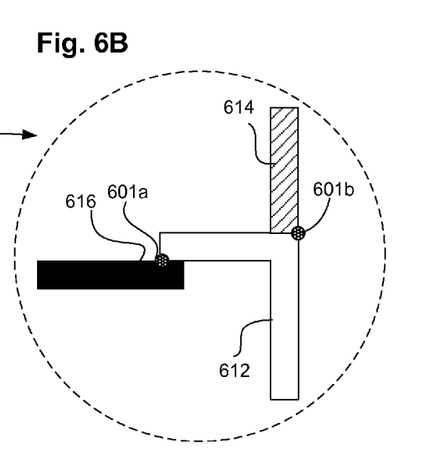

FIGS. 6A-6B illustrate another embodiment of a biostimulator 600, which is a variation of biostimulator 300 illustrated above in FIGS. 3A-3C. In FIGS. 6A-6B, lid 616 and feedthrough 610A can be inserted from the bottom (or proximal end of the biostimulator) and welded to the proximal facing surface of cylindrical walls 612 with weld 601a. Dual weld redundancy may be achieved by welding walls 614 to walls 612 with weld 601b. This is in contrast to biostimulator 300 in which the lid is mounted flush against the inner portion of cylindrical walls.

Figure 7A:
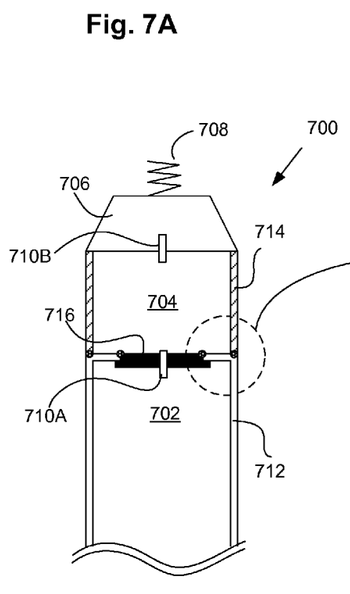
FIGS. 7A-7B illustrate yet another embodiment of an implantable medical device with dual-redundant welds.
Figure 7B:
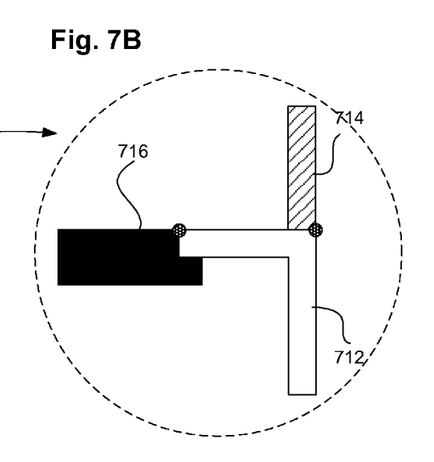

In another embodiment, shown in FIGS. 7A-7B, a similar concept is used except lid 716 contacts both the inner surface of cylindrical walls 712 at welds 701 as well as the proximal surface of the cylindrical walls. In this embodiment, the lid is thicker and is shaped with a flange to seat in the opening created in 712. This flange will provide self-centering as well as provide a backstop against weld penetration into the battery.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An implantable medical device, comprising:
    a battery disposed in a battery housing, the battery housing comprising a battery wall and a first lid, and the battery housing configured to operate as an electrode;
    a set of electronics disposed in an electronics housing, the set of electronics being electrically coupled to the battery and configured to control operation of the electrode;
    a first set of welds configured to hermetically join the battery wall, the first lid, and the electronics housing so as to hermetically seal the battery from the set of electronics; and
    a second set of welds configured to hermetically join the battery wall and electronics housing so as to seal the set of electronics and the battery from an exterior of the implantable medical device, wherein the first set of welds is disposed only on an interior of the implantable medical device and the second set of welds is disposed on the exterior of the implantable medical device.

2. The implantable medical device of claim 1, wherein the battery comprises a toxic component and wherein the first set of welds is configured to prevent the toxic component of the battery from leaking to the exterior of the implantable medical device when the second set of welds fails.

3. The implantable medical device of claim 1, wherein the battery housing is not surrounded by or enclosed in a separate housing.

4. The implantable medical device of claim 1, wherein the implantable medical device is a leadless cardiac pacemaker and wherein an external surface of the battery housing is also an external surface of the pacemaker.

5. The implantable medical device of claim 1, wherein the implantable medical device is a leadless cardiac pacemaker and the battery wall and electronics housing combine to form a cylindrical housing of the pacemaker.

6. The implantable medical device of claim 1, wherein:
the first lid is welded to a distal portion of the battery wall,
the battery housing further comprises a second lid welded to a proximal portion of the battery wall with a third set of welds to hermetically seal the proximal portion of the battery housing.

7. The implantable medical device of claim 6, further comprising a cap surrounding the second lid and welded to the battery housing with a fourth set of welds to provide dual-weld redundancy for the proximal end of the housing.

8. The implantable medical device of claim 1, wherein the first and second sets of welds are laser bead welds.

9. An implantable medical device, comprising:
a battery disposed in a battery housing, the battery housing comprising a battery wall and a first lid, the battery wall comprising an external surface of the implantable medical device;
a set of electronics disposed in an electronics housing and electrically coupled to the battery, the set of electronics configured to control operation of the implantable medical device;
a first set of welds configured to join the battery wall to the first lid to hermetically seal the battery from the set of electronics; and
a second set of welds configured to join the battery wall to the electronics housing to hermetically seal the set of electronics and the battery from an exterior of the implantable medical device, wherein the first set of welds is disposed only on an interior of the implantable medical device and the second set of welds is disposed on the exterior of the implantable medical device.

10. The device of claim 9, wherein the battery comprises a toxic component and wherein the first set of welds is configured to prevent the toxic component of the battery from leaking to an exterior of the implantable medical device when the second set of welds fails and the second set of welds is configured to prevent the toxic component of the battery from leaking to the exterior of the implantable medical device when the first set of welds fails.

11. The device of claim 9, wherein the battery housing is not surrounded by or enclosed in a separate housing.

12. The device of claim 9, wherein:
the battery wall comprises a lip, the lip comprising an inner portion disposed only on an interior of the implantable medical device and an outer portion disposed on an exterior of the implantable medical device,
the first lid is welded to the battery wall at the inner portion of the lip with the first set of welds to join the battery wall to the first lid and hermetically seal the battery from the set of electronics, and
the second set of welds is disposed on the exterior of the implantable medical device, wherein the second set of welds weld the battery wall and the electronics housing together at the outer portion of the lip.

13. The device of claim 9, wherein the battery wall and electronics housing combine to form a cylindrical housing of the device.

14. The device of claim 9, wherein the first set of welds is configured to hermetically seal the distal portion of the battery housing, wherein the device further comprises a second lid welded to a proximal portion of the battery housing only on the interior of the medical device with a third set of welds to hermetically seal the proximal portion of the battery housing.

15. The device of claim 14, further comprising a cap surrounding the second lid and welded to the battery housing with a fourth set of welds to provide dual-weld redundancy for the proximal end of the housing.

16. The device of claim 9, the battery housing further comprising a lip positioned near a distal end of the battery housing, the lip extending inwards from the external surface of the implantable medical device and then distally.

17. The device of claim 9, the battery housing further comprising an indentation positioned near a distal end of the battery housing, the indentation extending inwards from the external surface of the battery housing.

18. The device of claim 9, the battery housing further comprising a first lip positioned near a distal end of the battery housing and a second lip positioned near a proximal end of the battery housing, the first lip extending inwards from the external surface of the implantable medical device and then distally and the second lip extending inwards from the external surface of the implantable medical device and then proximally.

19. The device of claim 9, the battery housing further comprising a first indentation positioned near a distal end of the battery housing and a second indentation positioned near a proximal end of the battery housing, the first and second indentations extending inwards from the external surface of the housing.

20. The device of claim 9, wherein the first and second sets of welds are laser bead welds.

21. The device of claim 9, wherein the implantable medical device is an implantable cardiac device.

22. A leadless cardiac pacemaker, comprising:
a battery disposed in a battery housing, the battery housing comprising a battery wall and a lid, the battery housing configured to operate as an electrode;
a set of electronics disposed in an electronics housing, the set of electronics being electrically coupled to the battery and configured to control operation of the electrode, wherein:
the battery wall is welded to the lid and the electronics housing with a first set of welds, wherein the first set of welds is disposed only on an interior of the leadless cardiac pacemaker,
the electronics housing is welded to the battery wall with a second set of welds disposed on the exterior of the leadless cardiac pacemaker; and
a fixation device configured to attach the leadless cardiac pacemaker to human tissue.

23. The leadless cardiac pacemaker of claim 22, wherein the battery comprises an electrolyte, wherein the first set of welds is configured to hermetically seal the battery from the set of electronics, wherein the second set of welds is configured to hermetically seal the set of electronics and the battery from an exterior of the leadless cardiac pacemaker, and wherein the first and second welds are configured so that both the first and second set of welds must fail for the electrolyte to leak to the exterior of the leadless cardiac pacemaker.

24. The leadless cardiac pacemaker of claim 22, wherein first and second sets of welds are laser bead welds.

25. The leadless cardiac pacemaker of claim 22, wherein the battery wall is thicker than the electronics housing.

\* \* \* \* \*